United States Patent [19]

Brenneman et al.

[11] Patent Number: 5,160,341
[45] Date of Patent: Nov. 3, 1992

[54] RESORBABLE URETHRAL STENT AND APPARATUS FOR ITS INSERTION

[75] Inventors: Rodney A. Brenneman, Mission Viejo; Jay A. Lenker, Laguna Beach, both of Calif.

[73] Assignee: Advanced Surgical Intervention, Inc., San Clemente, Calif.

[21] Appl. No.: 610,543

[22] Filed: Nov. 8, 1990

[51] Int. Cl.$^5$ ............................................. A61M 29/00
[52] U.S. Cl. .................................. 606/198; 606/108; 623/12
[58] Field of Search ............... 606/191, 198, 192, 193, 606/194, 200, 108; 623/1, 12; 604/8; 128/6

[56] References Cited

U.S. PATENT DOCUMENTS

| | | | |
|---|---|---|---|
| 3,620,218 | 11/1971 | Schmitt | 128/334 |
| 3,887,699 | 6/1975 | Yolles | 424/19 |
| 4,512,338 | 4/1985 | Balko et al. | 128/1 |
| 4,531,933 | 7/1985 | Norton et al. | 604/8 |
| 4,553,545 | 11/1985 | Maass et al. | 128/341 |
| 4,650,488 | 3/1987 | Bays et al. | 623/12 |
| 4,660,560 | 4/1987 | Klein | 128/344 |
| 4,665,918 | 5/1987 | Garza et al. | 623/12 |
| 4,670,286 | 6/1987 | Nyilas et al. | 427/2 |
| 4,674,506 | 6/1987 | Alcond | 128/334 |
| 4,732,152 | 3/1988 | Wallsten et al. | 128/343 |
| 4,762,128 | 8/1988 | Rosenbluth | 128/343 |
| 4,768,507 | 9/1988 | Fischell et al. | 606/198 |
| 4,820,298 | 4/1989 | Leveen et al. | 623/1 |
| 4,886,062 | 12/1989 | Wiktor | 128/343 |
| 4,886,870 | 12/1989 | D'Amore et al. | 528/206 |
| 4,893,623 | 1/1990 | Rosenbluth | 606/192 |
| 4,913,141 | 4/1990 | Hillstead | 606/108 |
| 4,950,258 | 8/1990 | Kawai et al. | 604/281 |
| 4,990,155 | 2/1991 | Wilkoff | 606/198 |

*Primary Examiner*—John D. Yasko
*Assistant Examiner*—William Lewis
*Attorney, Agent, or Firm*—Klein & Szekeres

[57] ABSTRACT

A resorbable stent, particularly adapted for implantation in the penile urethra, comprises a helical coil formed from a filament of a biocompatible, biodegradable material that is resiliently deformable. The stent is compressible from a first diameter to a smaller second diameter, and restores itself substantially to its first diameter by its own resiliency when the compressing force is removed. Polymers of polylactic acid and polyglycolic acid are preferred materials. A device for inserting the stent has a first embodiment that includes a retractable sheath surrounding a rotatable rod journaled in a stationary bushing. The stent is mounted on the rod and the bushing so that relative rotation of the rod and bushing compresses the stent by coiling it more tightly. The sheath is inserted into the urethra with the stent compressed inside of it, and the retracted. The rod and bushing are then relatively rotated so as to uncoil the stent, which is restored to its first diameter. A shearing sleeve is actuated to detach the stent from the rod and the bushing. A second embodiment includes a plunger on which the stent is detachably mounted. The plunger is inserted through the sheath, thereby compressing the stent. When the stent is discharged through the distal end of the sheath into the urethra, the stent resiliently restores itself to its first diameter.

41 Claims, 3 Drawing Sheets

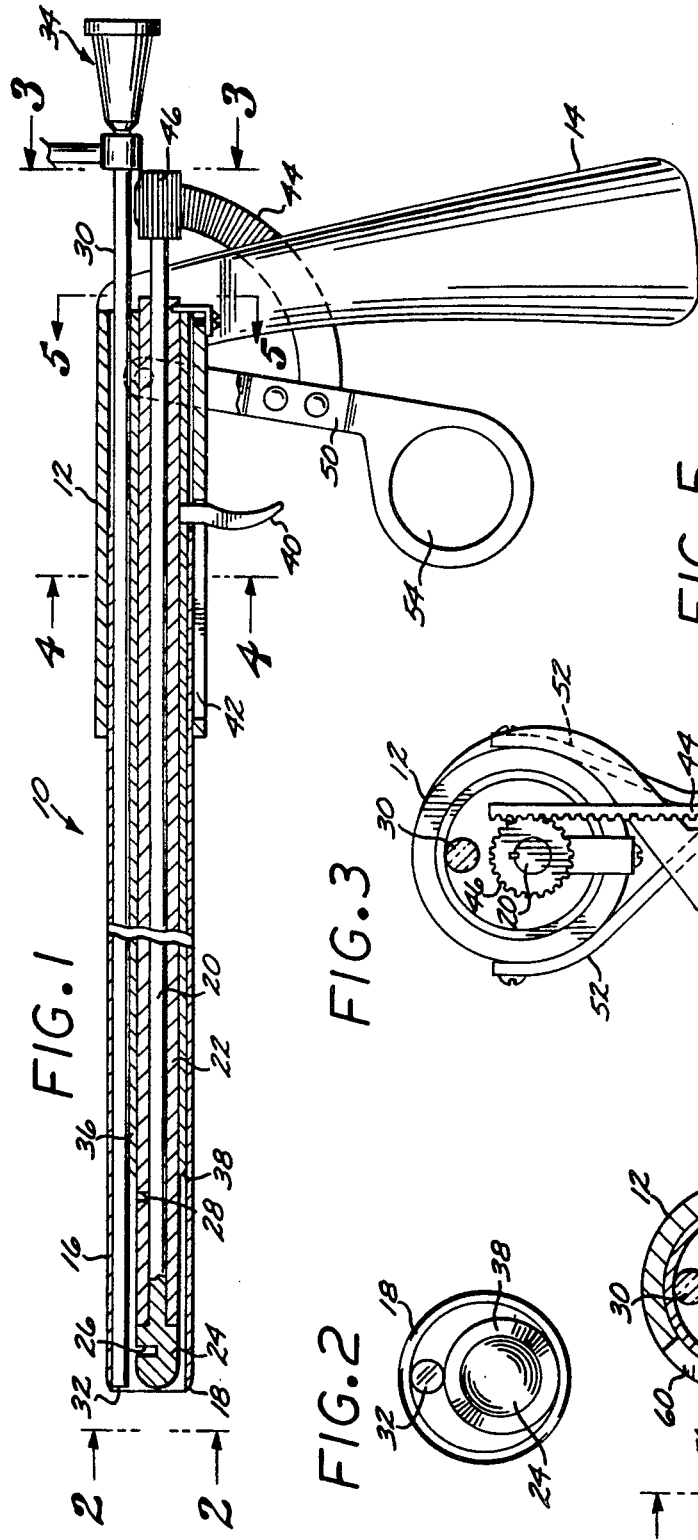

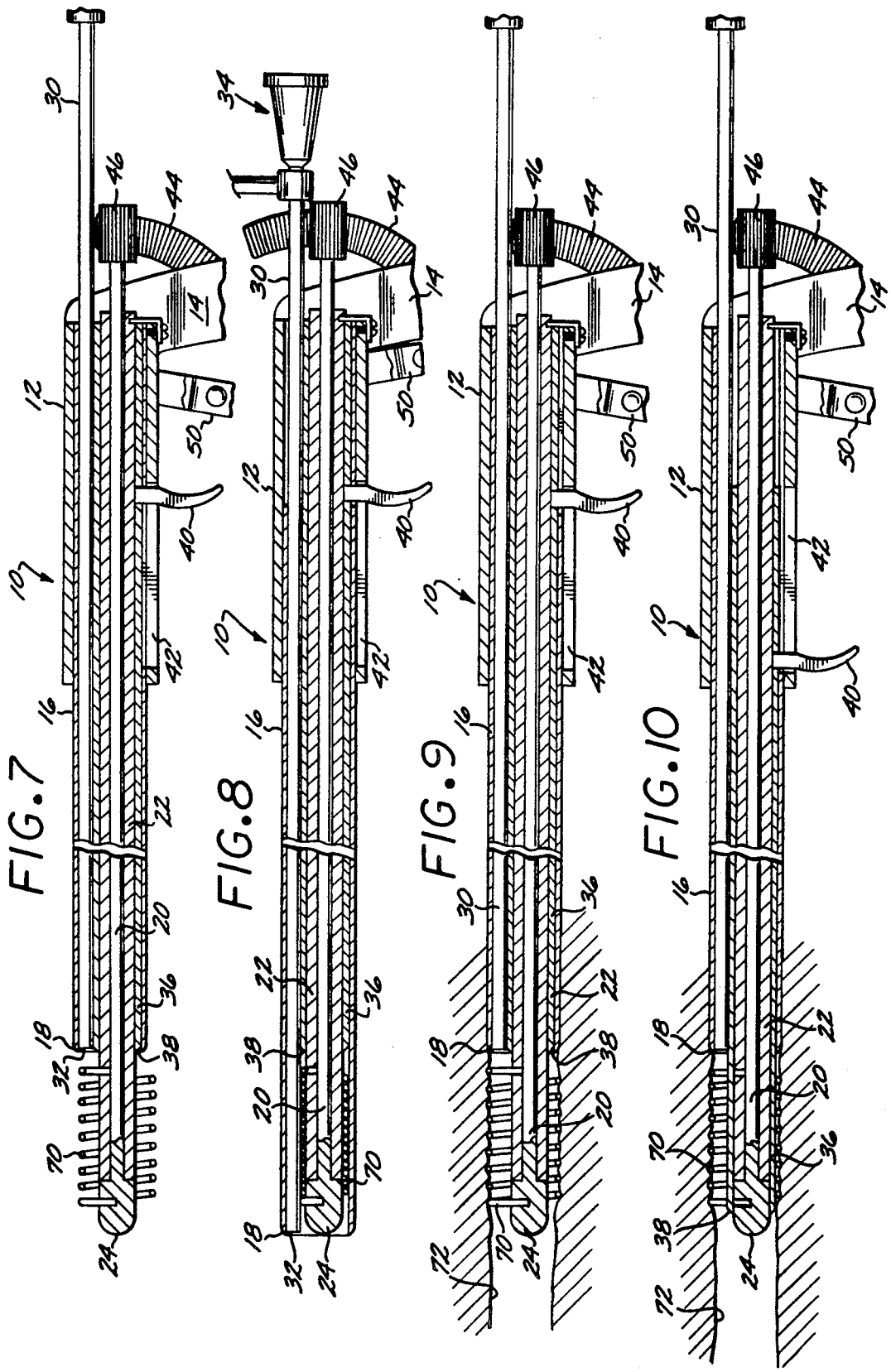

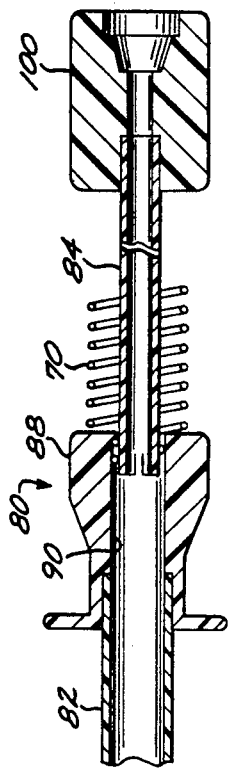
FIG.12
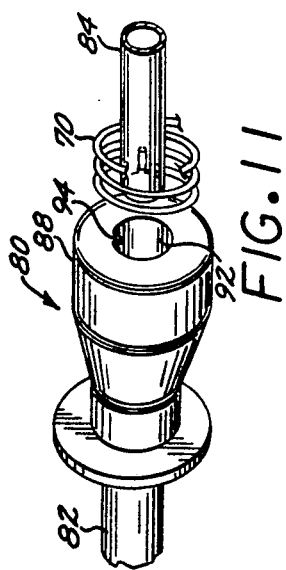
FIG.11
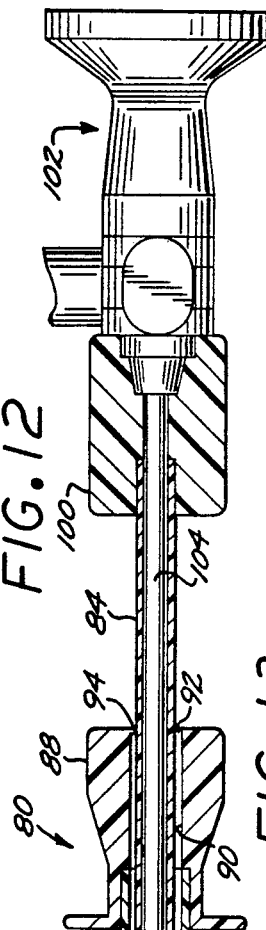
FIG.13
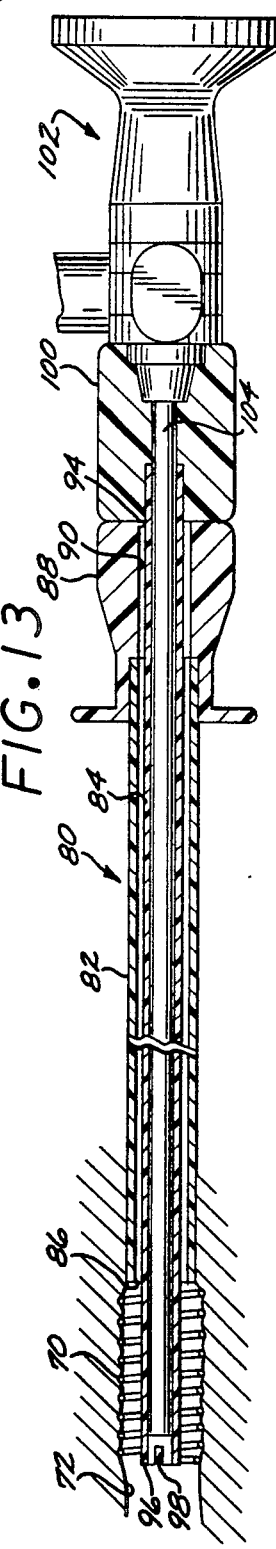
FIG.14
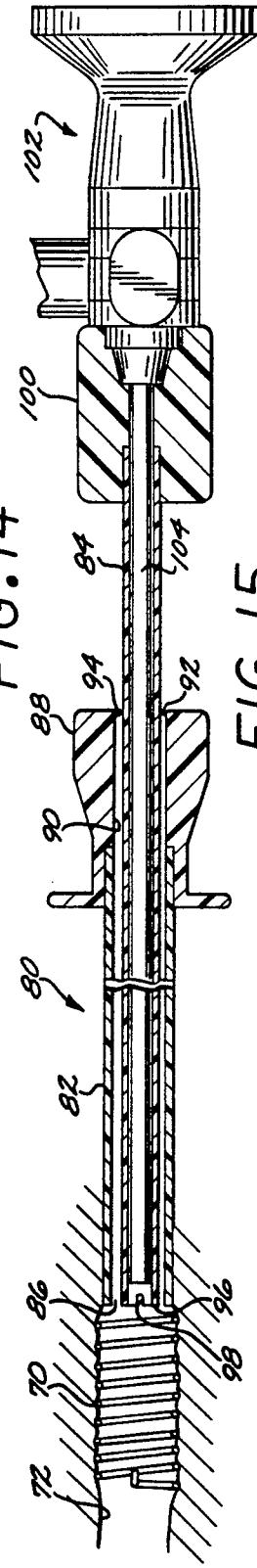
FIG.15

RESORBABLE URETHRAL STENT AND APPARATUS FOR ITS INSERTION

BACKGROUND OF THE INVENTION

This invention relates to the field of urological methods and devices, and more particularly to such methods and devices as are used in the treatment of urethral stenoses. More specifically, the present invention relates to a urethral stent, and to a method and apparatus for inserting and locating the stent in a human male urethra to treat the stenosis therein.

Stenosis (partial occlusion) of the human male urethra, resulting from disease or injury, is typically treated by surgery. Conventional surgical techniques, such as dilation or commissurotomy, however, often offer only temporary or partial relief, since it is not uncommon for the stenosis to reoccur. Alternative treatments for such stenoses or strictures, that wound maintain urethral patency for extended periods, have, therefore, been sought.

One approach for providing long-term relief for urethral stenoses is the implantation of a urethral stent. Urethral are known in the art, as exemplified by U.S. Pat. No. 4,762,128 —Rosenbluth and U.S. Pat. No. 4,893,623—Rosenbluth, both commonly assigned to the assignee of the present application. The Rosenbluth patents both relate to methods and apparatus for the treatment of prostatic hypertrophy, wherein a urethral stenosis caused by a hypertrophied prostate gland is relieved by the implantation of a stent in the stenotic region of the urethra. The stents disclosed in the Rosenbluth patents, however, are in the form of radially expandable metallic tubes that are specifically adapted for implantation in the prostatic region of the urethra by means of a balloon catheter, and that, once in place, can withstand the radial pressures exerted by the hypertrophied prostate. Such stents may be less well-suited for implantation in the penile portion of the urethra (where many strictures occur), where less radial rigidity is needed, and where greater flexibility may be desired.

An alternative stent configuration is that of a helically-coiled spring, such as that disclosed in U.S. Pat. No. 4,553,545 —Maass et al. The helically-coiled stent disclosed in the Maass et al. patent is made of a stainless steel or the like, and is specifically adapted for implantation as an intravascular prosthesis. To this end, the Maass et al. patent discloses a device for implanting the stent in a blood vessel. This implantation device, however, is not suitable for implantation of the stent in a bodily lumen, such as the urethra, for a number of reasons, including the lack of means for visualizing the location of the stent within the enclosed lumen during implantation.

The particular physiology and structure of the penile urethra make it desirable to maximize the suppleness and flexibility of the stent, without sacrificing its ability to restore urethral patency by radially expanding the stenotic region To this end, certain biocompatible polymeric materials may offer significant advantages over the metallic materials disclosed in the Rosenbluth and Maass patents discussed above.

Among such polymeric materials, there exist a number of biodegradable or resorbable polymers that, upon implantation, gradually are absorbed by the body and replaced by living tissue, or that, when implanted in the urethra, would be dissolved by the urine flowing therethrough. At least two such materials are known and are widely-used for implanted devices: Polyglycolic Acid (PGA) and Polylactic Acid (PLA). See, for example, U.S. Pat. No. 3,620,218 —Schmitt et al. (PGA); and U.S. Pat. No. 3,887,699 —Yolles (PGA and PLA). U.S. Pat. No. 4,674,506—Alcond discloses an anastamosis stent made of PGA.

U.S. Pat. No. 4,950,258 —Kawai et al. discloses a coil-shaped molded article, made from homopolymers or copolymers of lactides or glycolides, that can be used as a biodegradable vascular implant to open up an obstructed blood vessel. The coiled article would be deformed for insertion into the blood vessel, and then heated. The application of heat would cause the article to return to its original shape. Depending on the specific shape and composition of the article, and the processes used for forming it into its original shape and giving it a "shape memory", temperatures in the range of 36 degrees Centigrade to 65 degrees Centigrade would apparently need to be applied to restore the article to its original shape in 10 seconds or less. The need to apply heat for shape restoration is disadvantageous, because it would complicate the insertion procedure, would require specialized heating implements (not disclosed in the Kawai et al. patent) during insertion, and would require care not to exceed a degree of heating (temperature and time duration) that could result in tissue damage.

As yet, the prior art has not contemplated the use of bioresorbable materials in the formulation of a helically-coiled urethral stent that does not depend upon the application of heat for shape restoration, nor has there been developed a suitable apparatus or method for the implantation of a helically-coiled stent in the penile urethra.

SUMMARY OF THE INVENTION

Broadly, the present invention is an apparatus for relieving stenosis of the penile urethra, comprising a biodegradable, or resorbable, urethral stent, formed in the shape of a single or multiple helical coil that is resiliently deformable; and a device that includes means for (a) resiliently compressing the stent prior to insertion into the urethra; (b) inserting the compressed stent into the urethra in the vicinity of the stenosis, using direct visualization for positioning ; and (c) releasing the stent in the selected location in the urethra, allowing the stent to be restored to its original shape either through its natural resilience, or by forced expansion (or a combination thereof), thereby relieving the stenosis.

More specifically, the stent, in the preferred embodiment of the invention, is formed from a biodegradable lactide homopolymer having an inherent viscosity of approximately 2.2. The stent would maintain structural integrity for at least about one month, and, preferably, for about three to nine months. When formed into a coil shape, as by extrusion or molding, the resultant article is resiliently compressible, so that the coil has an uncompressed first diameter, and a compressed second diameter smaller than the first diameter. When the compressive force is released, the coil can resiliently spring back substantially to the first diameter.

The stent length is ideally sized to equal or slightly exceed the length of the stricture. The stent is adapted for insertion into the urethra under direct endoscopic visualization, so that the stent fully supports the portion of the urethra that is narrowed by the stricture.

The device for inserting and locating the stent in the urethra has two preferred embodiments. In the first preferred embodiment, the inserting device includes a rotatable rod or core, coaxially surrounded by a stationary tubular bushing, the core having a head that is left exposed at one end of the bushing. The bushing, in turn, is surrounded by a retractable tubular sheath. The stent, in its normal shape (first diameter) has one end fixed to the core head and the other end fixed to the bushing. Core rotation means (preferably a rack and pinion mechanism for operator convenience) are provided to rotate the core with respect to the bushing, thereby more tightly coiling the stent until it assumes its compressed form (second diameter).

With the stent in its compressed form, the sheath of the insertion device, in its extended position (covering the stent and the core head) is inserted into the urethra, with the help of visualization provided by a lens assembly and optical guide carried within (or along the side of) the sheath and extending axially along it. When the end of the sheath is located at the desired implantation site of the stent (i.e., proximate the stenosis), the sheath is withdrawn (by means of a lever, for example), and the core is counter-rotated with respect to the bushing, so as to unwind the stent back to its normal shape (first diameter).

A tubular sleeve with an annular shearing edge is disposed coaxially around the bushing, and is adapted for axial movement with respect to the bushing. When the stent is properly located and unwound to its original shape, the sleeve is moved forwardly so that the shearing edge severs the stent from its attachment points on the bushing and the core. The device is then removed from the urethra, leaving the stent in place at the stenosis site. Alternatively, the ends of the stent could be held by a clamping mechanism on the core and the bushing, which would allow the stent to be released when desired.

In a second preferred embodiment, the insertion device comprises a hollow, tubular sheath and a hollow, tubular plunger that is insertable into the sheath. The outer end of the sheath is terminated by a hub assembly that includes a central bore, continuous and axially aligned with the interior of the sheath, and a threading guide at the outer opening of the bore. The plunger has a first, or inner end to which one end of the stent is attached, the stent extending over a portion of the plunger proximate its inner end. The opposite, or outer end of the plunger is provided with a plunger hub assembly that mates with a lens assembly. The lens assembly, in turn, is optically coupled an optical guide that extends axially through the interior of the plunger.

In using the insertion device in accordance with the second preferred embodiment, the sheath is first inserted into the urethra, using an obturator, which is subsequently removed. The inner end of the plunger, which carries the stent, is placed adjacent to the bore opening in the sheath hub assembly, so as to engage the stent with the threading guide. The plunger is then rotated and pushed axially into the sheath hub assembly so as to thread the stent into the bore, thereby compressing the stent from its normal shape (first diameter) into its compressed shape (second diameter). The plunger is then pushed axially through the sheath, stopping short of the inner end of the sheath, so that the stent remains covered by the sheath. Using the lens assembly and the optical guide for visualization into the urethra, the inner end of the sheath is positioned to the desired implantation site. When the inner end of the sheath is properly located, the plunger is pushed inwardly again to push the stent out of the sheath. No longer radially constrained by the sheath, the stent expands to its original shape (first diameter) at the implantation site. The sheath and plunger are then withdrawn from the urethra.

Both of the preferred embodiments of the insertion device exhibit significant advantages. For example, both embodiments can be employed, perhaps with relatively minor modifications, to install a helically-coiled implant in bodily passages other than the urethra. Likewise, with only minor modifications (if any), both embodiments may be used to install helically-coiled implants formed of any resilient, biocompatible material, not just those of a biodegradable polymer. Finally, both embodiments offer a heretofore unrealized facility in the installation of a urethral stent in the penile portion of the male urethra.

These and other advantages will be more fully appreciated from the detailed description of the invention that follows.

BRIEF DESCRIPTION OF THE DRAWINGS

FIG. 1 is a side elevational view, partially in cross section, of a first preferred embodiment of a urethral stent insertion device, in accordance with the present invention;

FIG. 2 is a front elevational view of the device of FIG. 1, taken along line 2—2 of FIG. 1;

FIG. 3 is a view taken along line 3—3 of FIG. 1;

FIG. 4 is a cross sectional view taken along line 4—4 of FIG. 1;

FIG. 5 is a cross sectional view taken along line 5—5 of FIG. 1;

FIG. 6 is a fragmentary side elevational view of the of FIG. 1, taken along line 6—6 of FIG. 4;

FIG. 7 is a partial cross sectional view, similar to that of FIG. 1, showing the device with the sheath withdrawn and a urethral stent attached to the rotatable core and the stationary prior to insertion of the stent in a patient's urethra;

FIGS. 8, 9, and 10 are partial cross sectional Views, similar to that of FIG. 7, showing the steps in the process of inserting the stent into the urethra;

FIG. 11 is fragmentary perspective view of a second preferred embodiment of a stent insertion device, in accordance with the present invention, showing the outer portion of the sheath with the sheath hub assembly, and the inner end of the plunger with a urethral stent attached to it;

FIG. 12 is a longitudinal cross sectional View of the device of FIG. 11, showing the step of inserting the plunger and the stent into the sheath; and FIGS. 13, 14, and 15 are elevational views, partially in longitudinal cross section, showing the steps of inserting the stent into a patient's urethra using the device of FIG. 11.

DETAILED DESCRIPTION OF THE INVENTION

Referring first to FIGS. 1 through 6, a urethral stent insertion device 10, in accordance with a first preferred embodiment of the invention is shown. The device 10 includes a hollow, tubular body 12 that is integral with a downwardly extending handle 14, the latter resembling a pistol grip in configuration.

Fitted into the body is one end of an elongate, hollow, tubular sheath 16, the other end of which (designated, for the purposes of this disclosure, as the distal end) terminates in a tapered tip 18 surrounding a distal opening. As explained below, the sheath 16 is axially movable between an extended position, shown in FIG. 1, and a withdrawn position, in which it is moved proximally (i.e., toward the handle 14). Longitudinally disposed within the sheath is a rotatable rod or core 20, which is journaled within an elongate, tubular, stationary bushing 22. The core 20 has a distal end that terminates in a knob or head 24 that is exposed from the distal end of the bushing 22, the bushing thereby extending proximally from the head 24. The head 24 is provided with a first radial slot 26, and the bushing 22 is provided with a similar second radial slot 28 spaced from its distal end. The radial slots 26 and 28 serve as first and second attachment points, respectively, for a stent, as explained below.

Also longitudinally disposed in the sheath 16 is an optical guide 30, having a distal end 32 near the tip 18 of the sheath, and a proximal end that is adapted for attachment to a lens assembly 34. The optical assembly 30, 34 provides direct visualization through the sheath 16.

A tubular sleeve 36, with an annular shearing edge 38 at its distal end, is disposed coaxially around the bushing 22, and is adapted to slide axially along the bushing. To this end, a downwardly-depending lever 40 is provided, extending through a longitudinal slot 42 in the bottom of the housing 12. The purpose of the sleeve 36 will be explained below.

As mentioned above, the core 20 is rotatable with respect to bushing 22. A variety of mechanisms can be used to effect this rotation, but in the preferred embodiment, a rack and pinion mechanism is used. The rack and pinion mechanism comprises an arcuate rack 44 that operatively engages a pinion gear 46 attached to the proximal end of the core 20. The rack 44 subtends an arc of slightly more than 90 degrees, passing through a cut-out 48 on one side of the handle 14. The lower end of the rack 44 is attached to a core actuation lever 50. The core actuation lever 50 has a bifurcated upper portion 52 that is pivotally attached to the housing 12, as best shown in FIG. 3. The lower end of the core actuation lever is advantageously provided with a finger hole 54 to facilitate moving the rack 44 up and down to rotate the pinion gear 46 (and thus the core 20) in either direction.

As previously mentioned, the sheath 16 is adapted for longitudinal or axial movement with respect to the housing 12. As shown in FIGS. 4 and 6, a pin 56 extends laterally from the portion of the sheath enclosed within the housing, through a longitudinal slot 58 in the housing. The sheath is withdrawn or retracted from its extended position of FIG. 1 by pulling it proximally, so that the pin 56 moves proximally in the slot 58. The slot 58, at its distal end, advantageously has a downward extension 60 that retains the pin 56 (upon a slight rotation of the sheath) when the sheath is in its fully extended position, thereby locking the sheath 16 in its extended position to facilitate insertion of the sheath into the urethra, as described below.

As shown in FIGS. 7 through 10, the above-described embodiment of a stent insertion device is advantageously used to install a helically-coiled urethral stent 70 inside a patient's penile urethra 72. In accordance with a preferred embodiment of the invention, the stent 70 is a coiled filament of a biocompatible and biodegradable (resorbable) polymer, preferably formed by extrusion. Suitable materials include polylactic acid (PLA) homopolymers, polyglycolic acid (PGA) homopolymers, and copolymers of PLA and PGA. A specific example of a suitable material is a PLA homopolymer marketed by Henley Chemicals, Inc., of Montvale, N.J., under the trade name "RESOMER L 208", which has an inherent viscosity of approximately 2.2. Depending upon the particular application and the needs of the specific patient, the diameter of the filament that forms the stent may be in the range of approximately 20 to 40 mils (approximately 0.5 to 1.0 mm).

The material of the stent should be selected for suitable resilient deformability. That is, a helically-coiled stent of such material should be capable of being deformably compressed, and then substantially restoring itself to its original size and shape by means of its own resiliency, without the need for the application of heat (other than, possibly, the ambient body temperature heat of the installation site). In a typical penile urethral stent, for example, the stent should be compressible from an original (first) diameter of approximately 36 French to a compressed (second) diameter of approximately 24 French, with the ability to restore itself substantially to the first diameter (36 French) when the compressing force is removed.

As shown in FIG. 7, the sheath 16 has been moved to its retracted position, as described above. A stent 70, of the type described above, is disposed coaxially at the proximal end of the core/bushing assembly, with a first end attached to the core head 24 at the core head attachment slot 26, and a second end attached to the bushing at the bushing attachment slot 28. The insertion device 10 can be delivered pre-loaded with the stent, or the physician can load the device immediately before the commencement of the insertion procedure. The stent should be retained in its uncompressed, original configuration until the insertion procedure is begun to avoid the stent's taking a "set" due to plastic deformation.

FIG. 8 shows the device with the sheath 16 in its extended position. In this Figure, the core actuation lever 50 has been pulled toward the handle 14 (proximally), thereby causing the rack 44 to move upwardly in engagement with the pinion gear 46, causing the latter to rotate in a first direction, thereby likewise rotating the core 20 with respect to the bushing 22. By virtue of the rack and pinion mechanism, a relatively small movement of the handle will result in multiple rotations of the core. The rotation of the core with respect to the bushing causes the stent to become more tightly wound, thereby compressing the stent from its original (first) diameter to its compressed (second) diameter. The device is now ready for insertion into the urethra, the tapered tip 18 of the sheath 16 facilitating the insertion. Visualization of the urethra provided by the lens assembly 34 and the optical guide 30 helps the physician properly locate the distal end of the sheath at the site of the urethral stenosis to be treated.

In FIG. 9, the sheath 16 is shown as having been inserted into the urethra 72, and retracted, as previously described, to expose the stent from the distal opening of the sheath. At this time, the core actuation lever 50 is pushed distally (away from the handle 14), pulling the rack 44 downwardly in engagement with the pinion gear 46, thereby counter-rotating the pinion gear 46 and the core 20 in the opposite direction from that previously described. This counter-rotation causes the stent to unwind, the resilience of the stent allowing it to assume, once again, substantially its original (first) diameter. The physician can continue to visualize the stent installation through the optical system 30,34, and, if necessary, rewind the stent, and adjust the position of the stent to relocate the stent with respect to the stenosis.

Finally, as shown in FIG. 10, with the sheath 16 in its retracted position, the sleeve-actuating lever 40 is pushed distally (away from the handle 14) through the housing slot 42, causing the sleeve 36 to move distally toward the core head 24. As it does so, its shearing edge 38 shears the connections between the stent and the bushing and between the stent and the core head, thereby discharging the stent from the insertion device. The insertion device is then withdrawn from the urethra, leaving the stent in place at the stenosis site to relieve the stenosis.

Turning now to FIGS. 11 through 15, a urethral stent insertion device 80, in accordance with a second preferred embodiment of the invention is shown. This embodiment comprises elongate, hollow, tubular sheath 82; an elongate, hollow, tubular plunger 84 that is insertable through the interior of the sheath 82; and an optical assembly that is operatively associated with the plunger 84 and the sheath 82.

More specifically, the sheath 82 has an open distal end 86 and a proximal end to which is attached a hub 88. The hub 88 has central bore 90 that is axially aligned and continuous with the interior of the sheath, terminating in a proximal opening 92 (FIG. 11). Preferably, the internal diameter of the bore 90 is approximately the same as that of the sheath 82. Extending radially into the bore 90 near the proximal opening 92 is a threading guide 94, the purpose of which will be described below.

The plunger 84 has an outside diameter that is somewhat smaller than the inside diameter of the sheath 82, allowing the plunger to be inserted into the interior of the sheath with a predetermined circumferential clearance. The plunger has a distal tip 96 having an axial slot 98 that is dimensioned to receive one end of a helically-coiled stent 70. The stent 70 is thus carried coaxially on the distal end of the plunger 84, as shown in FIGS. 11 and 12. The stent 70 may advantageously be the same type of stent as that which has previously been described herein.

The proximal end of the plunger 84 is provided with a hub 100 that provides a fitting for the attachment of the abovementioned optical assembly. The optical assembly, in turn, comprises a lens assembly 102 that mates with the plunger hub 100, and an optical guide 104 that is dimensioned to pass through the interior of the plunger 84.

Use of the insertion device 80 is as follows:

The sheath 82 is introduced into the urethra 72, distal end 86 first, by an obturator (not shown), of a type well-known in the art, the obturator then being removed. The distal end of the plunger 84, with the stent 70 attached to it (as described above), is then inserted into the proximal opening 92 of the sheath hub 88, with the stent 70 being engaged by the threading guide 94, as shown in FIGS. 11 and 12. The plunger is then threaded into the central bore 90 of the sheath hub 88, and then into the interior of the sheath 82, as shown in FIG. 13. Because the internal diameters of the bore 90 and the sheath 82 are smaller than the normal (first) diameter of the stent 70, this threading action causes the stent to be captured between the plunger 84 and the sheath 82, and thus resiliently compressed to its smaller second diameter.

When the stent has been passed into the sheath 82, the optical guide 104 is inserted into the interior of the plunger, until the lens assembly 102 is coupled to the plunger hub 100, as shown in FIG. 13. At this point, the stent is still retained totally within the sheath 82. The visualization provided by the optical guide 104 and the lens assembly 102 allows the physician to locate distal end 86 of the sheath and move it to the desired location with respect to the implantation site. When the sheath has been properly located, the plunger is pushed further through the sheath, until the stent is discharged from the distal end 86 of the sheath. As shown in FIG. 14, once the stent is clear of of the sheath, it resiliently restores itself to substantially its first diameter within the urethra.

As shown in FIG. 15, the plunger 84 and the optical assembly 102, 104 are then removed from the sheath, and, finally, the sheath is removed from the urethra, leaving the stent in place.

The embodiment of FIGS. 11 through 15 offers the advantage of simplicity of construction and use, and is, therefore, especially adapted for disposability (at least with regard to the sheath and the plunger). Like the previously-described first embodiment, the second embodiment, while well-suited for insertion of a stent in the penile urethra, can easily be adapted for inserting a stent into other bodily lumens and passages. Moreover, both of the above-described embodiments can be used with helically-coiled stents formed of a variety of materials, not just the bioresorbable polymers describe herein. For example, suitable stents can be made of any of several well-known biocompatible (but not bioresorbable) polymers or metals that exhibit sufficient resiliency to restore themselves to their original shape and size, after having been compressed.

Although two preferred embodiments of the invention have described herein, variations and modifications may suggest themselves to those skilled in the pertinent arts. For example, as alluded to above, a variety of specific mechanisms may be contemplated for rotating the core 20 in the first embodiment. Similarly, the mechanism for severing the stent from the core and the bushing 22 may assume a number of forms, as can the sheath withdrawal mechanism. Likewise, the optical assemblies used in either of the above-described embodiments can be modified to suit particular needs and applications. In addition, the ends of the stent can be configured to both attach the stent to the insertion device, and to be engaged by a device for removing the stent, if desired. Also the stent can be coated or impregnated with an antimicrobial agent, such as silver oxide, to minimize the risk of infection. Similarly, a resorbable stent impregnated with a drug could be used as a drug delivery vehicle. Such variations and modifications should be considered within the spirit and scope of the invention, as defined in the claims that follow.

What is claimed is:

1. A device for inserting a helically-coiled stent, formed of a resiliently-deformable, biocompatible material, into a bodily lumen of a patient, comprising:

an elongate, hollow, tubular sheath adapted for insertion into the lumen, the sheath having an open distal end;

first means, engageable with the stent, for (a) carrying the stent within the sheath, and (b) discharging the stent into the lumen through the distal end of the sheath; and second means, operatively connected to the sheath and engageable with the stent while the stent is engaged with the first means, for resiliently compressing the stent from an uncompressed first diameter to a compressed second diameter when the stent is inserted into the sheath;

whereby the stent is resiliently restored to substantially its first diameter when discharged through the distal end of the sheath into the lumen.

2. The device of claim 1, further comprising:
optical means, axially disposed within the sheath, for allowing he visualization of the lumen through the sheath when the sheath is inserted thereinto.

3. The device of claim 1, wherein the sheath is axially movable between an extended position and a retracted position, and wherein the first means comprises an elongate rod disposed axially within the interior of the sheath, the elongate rod having a distal portion on which the stent is carried, the distal portion being exposed through the distal end of the sheath when the sheath is in its retracted position.

4. The device of claim 3, wherein the elongate rod includes a head at its distal end, the head being adapted for the attachment of a first end of the stent, and wherein the second means comprises:
a tubular bushing coaxially surrounding a portion of the elongate rod extending proximally from the head, the bushing being adapted for the attachment of a second end of the stent; and
rotational means for causing relative rotation between the bushing and the elongate rod;
whereby, when the stent is attached to the head and the bushing, the relative rotation of the bushing and the elongate rod in a first direction compresses the stent from its first diameter to its second diameter, and the relative rotation of the bushing and the elongate rod in a second direction restores the stent from its second diameter substantially to its first diameter.

5. The device of claim 4, wherein the rotational means comprises means connected to an end of the elongate rod opposite the head for selectively rotating and counter-rotating the elongate rod axially relative to the bushing.

6. The device of claim 4, wherein the rotational means comprises:
a pinion gear connected to an end of the elongate rod opposite the head;
a rack operatively engaging the pinion gear and movable with respect to the pinion gear in a first direction to rotate the pinion gear, and in a second direction to counter-rotate the pinion gear; and
manually actuable means, operatively connected to the rack, for selectively moving the rack in the first and second directions.

7. The device of claim 4, further comprising:
detachment means for detaching the stent from the bushing and the head to discharge the stent into the lumen.

8. The device of claim 7, wherein the detachment means comprises:
a tubular sleeve disposed coaxially around the bushing and adapted to slide axially thereon between a distal position and a proximal position;
a distal edge on the sleeve adapted for shearing the connections between the stent and the bushing and between the stent and the head when the sleeve is moved from its proximal position to its distal position; and
manually operable means for selectively moving the sleeve between its proximal and distal positions.

9. The device of claim 1, wherein the sheath has an internal diameter that is smaller than the first diameter of the stent, and wherein:
the first means comprises an elongate plunger, sized to be insertable into the interior of the sheath with a predetermined circumferential clearance, the plunger having a distal portion adapted for removably carrying the stent coaxially thereon; and
the second means comprises guide means, disposed at the proximal end of the sheath and engageable with the stent, for reducing the diameter of the stent to substantially the internal diameter of the sheath a the plunger is inserted into the sheath;
whereby the stent is passed through the interior of the sheath by the plunger and discharged from the distal end of the sheath into the lumen, where the stent is resiliently restored substantially to its first diameter.

10. The device of claim 9, wherein the plunger comprises an elongate hollow tube, and wherein the device further comprises:
Optical means that includes an optical guide adapted for passage through the interior of the plunger.

11. Apparatus for treating a stenosis in a bodily lumen, comprising:
a stent formed as a substantially helical coil of biocompatible, resiliently deformable material; and
insertion means, insertable into the lumen, for (a) resiliently compressing the stent from a first diameter to a smaller second diameter, (b) inserting the compressed stent into the lumen in the vicinity of the stenosis, and (c) releasing the stent, substantially restored to its first diameter, into the lumen at the site of the stenosis, the restoration of the stent to substantially its first diameter being at least partially the result of the resilient deformability of the stent.

12. The apparatus of claim 11, wherein the stent is formed from a biodegradable material.

13. The apparatus of claim 12, wherein the material is selected from the group consisting of polylactic acid homopolymers, polyglycolic acid homopolymers, and copolymers of polylactic acid and polyglycolic acid.

14. The apparatus of claim 13, wherein the stent is formed from a polylactic acid homopolymer.

15. The apparatus of claim 11, wherein the stent is formed from a filament of material having a diameter in the range of approximately 0.5 to 1.0 mm.

16. The apparatus of claim 11, further comprising:
optical means, disposed axially within the insertion means, for allowing the visualization of the lumen through the insertion means when the insertion means is inserted into the lumen.

17. The apparatus of claim 11, wherein the insertion means comprises:
an elongate, hollow, tubular sheath adapted for insertion into the lumen, the sheath having an open distal end;
first means, engageable with the stent, for (a) carrying the stent within the sheath, and (b) discharging the stent into the lumen through the distal end of the sheath; and second means, operatively connected to the sheath and engageable with the stent while the stent is engaged with the first means, for resiliently compressing the stent from an uncompressed first diameter to a compressed second diameter when the stent is inserted into the sheath;

whereby the stent is resiliently restored to substantially its first diameter when discharged through the distal end of the sheath into the lumen.

18. The apparatus of claim 17, wherein the sheath is axially movable between an extended position and a retracted position, and wherein the first means comprises an elongate rod disposed axially within the interior of the sheath, the elongate rod having a distal portion on which the stent is carried, the distal portion being exposed through the distal end of the sheath when the sheath is in its retracted position.

19. The apparatus of claim 18, wherein the elongate rod includes a head at its distal end, the head being adapted for the attachment of a first end of the stent, and wherein the second means comprises:

a tubular bushing coaxially surrounding a portion of the elongate rod extending proximally from the head, the bushing being adapted for the attachment of a second end of the stent; and rotational means for causing relative rotation between the bushing and the elongate rod;

whereby, when the stent is attached to the head and the bushing, the relative rotation of the bushing and the elongate rod in a first direction compresses the stent from its first diameter to its second diameter, and the relative rotation of the bushing and the elongate rod in a second direction restores the stent from its second diameter substantially to its first diameter.

20. The apparatus of claim 19, wherein the rotational means comprises means connected to an end of the elongate rod opposite the head for selectively rotating and counter-rotating the elongate rod axially relative to the bushing.

21. The apparatus of claim 19, wherein the rotational means comprises:

a pinion gear connected to an end of the elongate rod opposite the head;

a rack operatively engaging the pinion gear and movable with respect to the pinion gear in a first direction to rotate the pinion gear, and in a second direction to counter-rotate the pinion gear; and manually actuable means, operatively connected to the rack, for selectively moving the rack in the first and second directions.

22. The apparatus of claim 19, further comprising:

detachment means for detaching the stent from the bushing and the head to discharge the stent into the lumen.

23. The apparatus of claim 22, wherein the detachment means comprises:

a tubular sleeve disposed coaxially around the bushing and adapted to slide axially thereon between a distal position and a proximal position;

a distal edge on the sleeve adapted for shearing the connections between the stent and the bushing and between the stent and the head when the sleeve is moved from its proximal position to its distal position; and manually operable mean for selectively moving the sleeve between its proximal and distal positions.

24. The apparatus of claim 17, wherein the sheath has an internal diameter that is smaller than the first diameter of the stent, and wherein:

the first means comprises an elongate plunger, sized to be insertable into the interior of the sheath with a predetermined circumferential clearance, the plunger having a distal portion adapted for removably carrying the stent coaxially thereon; and the second means comprises guide means, disposed at the proximal end of the sheath and engageable with the stent, for reducing the diameter of the stent to substantially the internal diameter of the sheath as the plunger is inserted into the sheath;

whereby the stent is passed through the interior of the sheath by the plunger and discharged from the distal end of the sheath into the lumen, where the stent is resiliently restored substantially to its first diameter.

25. The apparatus of claim 24, wherein the plunger comprises an elongate tube, and wherein the apparatus further comprises an optical guide adapted for passage through the interior of the plunger.

26. A method for treating a stenosis in a bodily lumen, comprising the steps of:

(1) inserting at least a portion of a sheath, including a distal end thereof, into the lumen, while the lumen is under direct visualization through the sheath;

(2) providing a helically coiled stent of resiliently deformable, biocompatible material;

(3) resiliently compressing the stent from an uncompressed first diameter to a smaller compressed diameter;

(4) while the stent is compressed to its smaller diameter, and while the lumen is under direct visualization through the sheath, passing the stent through the sheath into the lumen to the vicinity of the stenosis; and (5) while the lumen is under direct visualization through the sheath, discharging the stent, from the distal end of the sheath, into the lumen at the site of the stenosis, thereby allowing the stent to restore itself substantially to its uncompressed diameter, at least substantially as a result of its inherent resiliency.

27. The method of claim 26, wherein the stent is formed from a biodegradable material selected from the group consisting of homopolymers of polylactic acid, homopolymers of polyglycolic acid, and copolymers of polylactic acid and polyglycolic acid.

28. A method for treating a stenosis in a bodily lumen, comprising the steps of:

(1) providing a helically-coiled stent of resiliently deformable, biocompatible material, the stent being provided in an uncompressed first diameter, and removably attached to manually actuable coiling means for selectively coiling the stent more or less tightly;

(2) actuating the coiling means to coil the stent more tightly, thereby resiliently compressing the stent from the uncompressed first diameter to a compressed second diameter smaller than the first diameter;

(3) enclosing the stent within a sheath, near the distal end thereof, while maintaining the stent in its second diameter;

(4) inserting at least that portion of the sheath enclosing the stent into the lumen so as to locate the stent substantially at the site of the stenosis;

(5) withdrawing the sheath; and (6) restoring the stent substantially to its uncompressed first diameter at the site of the stenosis.

29. The method of claim 28, wherein the step of restoring comprises the steps of:

(a) actuating the coiling means to coil the stent less tightly to restore the stent substantially to its first diameter; and (b) removing the stent from the coiling means.

30. The method of claim 28, wherein the stent is formed from a biodegradable material selected from the group consisting of homopolymers of polylactic acid, homopolymers of polyglycolic acid, and copolymers of polylactic acid and polyglycolic acid.

31. The method of claim 28, wherein the step of inserting is performed under direct visualization of the lumen through the sheath.

32. The method of claim 31, wherein the steps of withdrawing and restoring are performed under direct visualization of the lumen through the sheath.

33. A device for inserting a helically-coiled stent, formed of a resiliently-deformable, biocompatible material, into a bodily lumen of a patient, comprising:

an elongate, hollow, tubular sheath adapted for insertion into the lumen, the sheath having an open distal end, the sheath being axially-movable between an extended position and a retracted position;

an elongate rod, disposed axially within the interior of the sheath, and having a distal portion that is exposed through the distal end of the sheath when the sheath is in its retracted position, the distal portion terminating in a head adapted for the removable attachment thereto of one end of the stent;

a tubular bushing coaxially surrounding a portion of the removable attachment thereto of a second end of the stent; and rotational means for causing relative rotation between the bushing and the rod;

whereby, when the stent is attached to the head and the bushing, the relative rotation of the bushing and the elongate rod in a first direction compresses the stent from a first diameter to a smaller second diameter, and the relative rotation of the bushing and the elongate rod in a second direction restores the stent from its second diameter substantially to its first diameter.

34. The device of claim 33, wherein the rotational means comprises means connected to an end of the elongate rod opposite the head for selectively rotating and counter-rotating the elongate rod axially relative to the bushing.

35. The device of claim 33, wherein the rotational means comprises:

a pinion gear connected to an end of the elongate rod opposite the head;

a rack operatively engaging the pinion gear and movable with respect to the pinion gear in a first direction to rotate the pinion gear, and in a second direction to counter-rotate the pinion gear; and manually actuable means, operatively connected to the rack, for selectively moving the rack in the first and second directions.

36. The device of claim 33, further comprising:

detachment means for detaching the stent from the bushing and the head to discharge the stent into the lumen 37. The device of claim 36, wherein the detachment means comprises:

a tubular sleeve disposed coaxially around the bushing and adapted to slide axially thereon between a distal position and a proximal position;

a distal edge on the sleeve adapted for shearing the connections between the stent and the bushing and between the stent and the head when the sleeve is moved from its proximal position to its distal position; and manually operable means for selectively moving the sleeve between its proximal and distal positions.

38. The device of claim 33, further comprising:

optical means, disposed axially within the sheath, for allowing the visualization of the lumen through the sheath when the sheath is inserted into the lumen.

39. A device for inserting a helically-coiled stent, formed of a resiliently-deformable, biocompatible material, into a bodily lumen of a patient, comprising:

an elongate, hollow, tubular sheath adapted for insertion into the lumen, the sheath having an open distal end;

an elongate plunger, sized to be insertable into the interior of the sheath with a predetermined circumferential clearance, the plunger having a distal portion adapted for removably carrying the stent coaxially thereon; and guide means, disposed at the proximal end of the sheath and engageable with the stent, for reducing the diameter of the stent from an uncompressed first diameter to substantially the internal diameter of the sheath as the plunger is inserted into the sheath;

whereby the stent is passed through the interior of the sheath by the plunger and discharged from the distal end of the sheath into the lumen, where the stent is resiliently restored substantially to its first diameter.

40. The device of claim 39, further comprising:

optical means, extending axially through the sheath, for allowing the visualization of the lumen through the sheath when the sheath is inserted into the lumen.

41. The device of claim 40, wherein the plunger comprises an elongate hollow tube, and wherein the optical means includes an optical guide adapted for passage through the interior of the plunger.

* * * * *

UNITED STATES PATENT AND TRADEMARK OFFICE
CERTIFICATE OF CORRECTION

PATENT NO.    : 5,160,341
DATED         : November 3, 1992
INVENTOR(S)   : Rodney A. Brenneman and Jay A. Lenker It is certified that error appears in the above-identified patent and that said Letters Patent is hereby corrected as shown below:

Column 1, line 24, after "Urethral" insert --stents--;

Column 4, line 37, after "the" insert --device--;

Column 4, line 39, after "that" insert --of--;

Column 4, line 42, after "stationary" insert --bushing,--;

Column 9, line 14, change "he" to --the--; and

Column 13, line 36 (Claim 33), after "the" insert --rod extending proximally from the head and adapted for the--.

Signed and Sealed this

Fifth Day of October, 1993

Attest:

BRUCE LEHMAN

Attesting Officer

Commissioner of Patents and Trademarks